United States Patent [19]
Gupta et al.

[11] Patent Number: 5,683,457
[45] Date of Patent: Nov. 4, 1997

[54] PRISMATIC INTRAOCULAR LENSES AND RELATED METHOD OF USING SUCH LENSES TO RESTORE VISION IN PATIENTS WITH CENTRAL FIELD LOSS

[75] Inventors: Amitava Gupta, Bethesda, Md.; Richard Mackool, Greenwich, Conn.

[73] Assignee: Prism Opthalmics, L.L.C., Roanoke, Va.

[21] Appl. No.: 647,228

[22] Filed: May 9, 1996

[51] Int. Cl.[6] ..................... A61F 2/16
[52] U.S. Cl. ..................... 623/6; 351/161
[58] Field of Search ............ 623/6, 5; 351/160 R, 351/161

[56] References Cited

U.S. PATENT DOCUMENTS

| | | | |
|---|---|---|---|
| 3,245,745 | 4/1966 | Hancock | 351/167 |
| 4,581,031 | 4/1986 | Koziol et al. | 623/6 |
| 4,641,934 | 2/1987 | Freeman | 623/6 X |
| 4,648,878 | 3/1987 | Kelman | 623/6 |
| 4,731,078 | 3/1988 | Stoy et al. | 623/6 |
| 4,779,972 | 10/1988 | Gottlieb | 351/177 |
| 4,786,657 | 11/1988 | Hammar et al. | 522/90 |
| 4,828,558 | 5/1989 | Kelman | 623/6 |
| 4,923,296 | 5/1990 | Erickson | 623/6 X |
| 4,932,970 | 6/1990 | Portney | 623/6 |
| 5,002,383 | 3/1991 | Sisler | 351/175 |
| 5,089,023 | 2/1992 | Swanson | 623/6 |
| 5,096,285 | 3/1992 | Silberman | 623/6 X |
| 5,151,723 | 9/1992 | Tajiri | 351/161 |
| 5,171,267 | 12/1992 | Ratner et al. | 623/6 |
| 5,443,507 | 8/1995 | Jacobi | 623/6 |

*Primary Examiner*—Mary Beth Jones
*Attorney, Agent, or Firm*—Finnegan, Henderson, Farabow, Garrett, and Dunner, L.L.P.

[57] ABSTRACT

A pair of intraocular lenses for restoring visual function to a patient with central field loss. The pair of intraocular lenses includes a first lens for implantation into a first eye of the patient to provide vision of targets located at a distance greater than five feet from the first eye and a second lens for implantation into a second eye of the patient to provide vision of targets at a distance less than twelve inches from the second eye. The first and second lenses each include a prismatic wedge for shifting retinal images to a functional portion of a retina of each respective first and second eye.

31 Claims, 3 Drawing Sheets

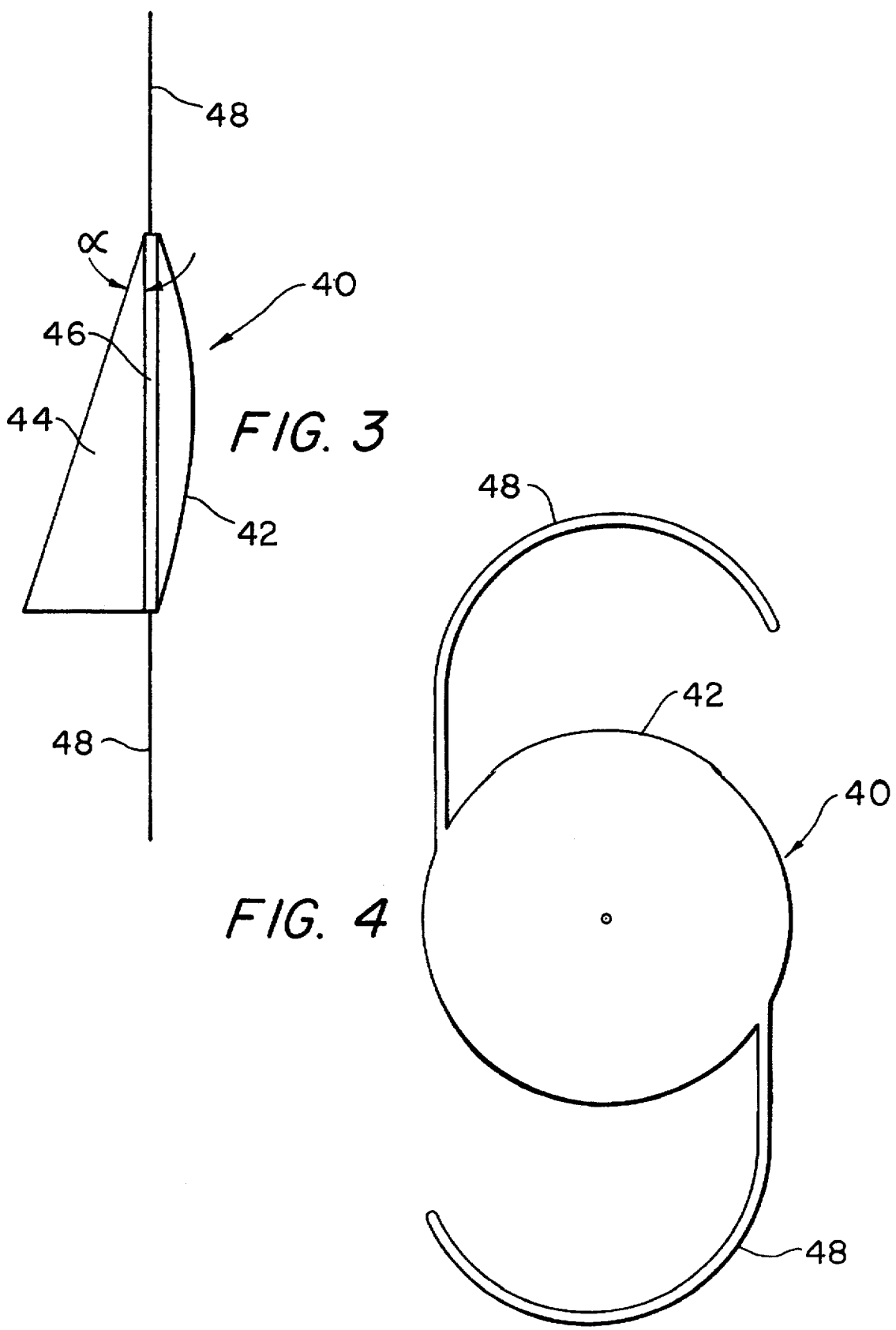

PRISMATIC INTRAOCULAR LENSES AND RELATED METHOD OF USING SUCH LENSES TO RESTORE VISION IN PATIENTS WITH CENTRAL FIELD LOSS

BACKGROUND OF THE INVENTION

1. Field of the Invention

The present invention relates to prismatic intraocular lenses and the related methods of using such lenses to restore vision in patients with macular degeneration and specifying particular prismatic intraocular lenses for use in such patients.

2. Description of the Related Art

As shown in FIG. 1, a normal eye 10 includes a cornea 12, an aqueous solution called the aqueous humor 14 behind cornea 12, an iris 16, a natural lens 18, ciliary sulcus 20, retina 22, macula 24 at the center of the retina, and fovea 26 at the center of macula 24. The cornea 12 and lens 18 cause an image 30 to form at fovea 26. Fovea 26 is a circular zone approximately 0.2–0.5 $mm^2$ in area. The image 30 formed at fovea 26 corresponds to a locus of fixation for providing acute vision. This locus of fixation helps to coordinate voluntary and involuntary head and eye movements required for daily activities, such as reading, driving, and dressing. Peripheral images are located around this locus of fixation.

A common cause of blindness in adults is macular degeneration. This retinal disease involves damage to the fovea so that the fovea is unable to process images. The a blind spot at the center of a patient's visual field. The patient is thus unable to read, drive, or perform other tasks that require the brain to reference the locus of fixation.

In most patients, even in those with advanced macular degeneration, the macula is not completely damaged, but retains healthy areas. However, the loss of the locus of fixation caused by the central blind zone leads to severe visual impairment and often to legal blindness, defined as visual acuity of 20/200 or less. The number of patients diagnosed with such severe visual impairment in the United States alone exceeds 2 million.

Intraocular lens implants have been devised to replace the natural lens of the eye and restore sight to damaged or diseased eyes. For example, compound intraocular lenses that combine different optical elements have been proposed. In such proposals, a diffractive/refractive lens implant includes a diffractive lens profile covering about half the effective lens area. Such a configuration allows about half of the incident light from distant objects and half of the incident light from near objects to enter the eye. Such a compound optic provides an ability to form on the retina a focused image of both distant objects and near objects.

Although both images are formed on the fovea, the brightness of the image in each case is reduced by about 50%, or the ratio of the light intensity assigned to each image. In certain cases, such a lens can be used to treat macular degeneration by providing sufficient image magnification so as to project the image over a retinal area more than that damaged by macular degeneration. Such an approach, however, does not shift the image to healthy portions of the retina.

Similar multifocal intraocular lenses incorporating two refractive zones also have been disclosed. For example, the use of a pair of bifocal intraocular lenses has been disclosed in which each of the pair of bifocal intraocular lenses incorporates a refractive element and a diffractive element. One of the lenses provides greater image intensity for the image of near objects, while the other lens provides greater image intensity for the image of distant objects. This approach has the advantage that the incident light can be apportioned or split between the two images in a continuous manner between the two lenses. The disadvantage is that the image is processed by two optical elements, each of which introduces its own aberrations and loss of image contrast so that the performance of the compound lens can be worse than either a diffractive or refractive lens.

Intraocular lenses incorporating a single refractive element also have been devised to shift the image from a damaged portion of the retina to a healthy area. In this respect, a prismatic intraocular lens that includes a convex lens portion for focusing light rays and a prism posterior to the convex lens for deflecting light away from the diseased center of the retina to a functional portion. The prismatic intraocular lens restores the central field vision to a patient.

Several considerations arise before such a prismatic intraocular lens can be prescribed for a patient with central field loss. For example, means to fixate the intraocular lens in the eye has to be developed in order to ensure that the lens does not rotate or tilt. Such displacements would cause the shifted retinal image to move, perhaps back to a zone which has become nonfunctional due to macular degeneration.

Addition of the prism wedge to the intraocular lens optic also causes an increase in the thickness of the optic. Due to the geometry of the eye, it is necessary to minimize the thickness of the prism wedge while remaining thick enough to redirect an image to a desired location on the retina. A methodology to prescribe particular prismatic intraocular lenses for patients also remains to be developed.

SUMMARY OF THE INVENTION

Accordingly, an object of this invention is to provide means to reduce the thickness of the prism wedge and, thereby, the overall thickness of the prismatic intraocular lens. An additional object is to minimize the susceptibility of rotation of the intraocular lens in the eye. A further object is to provide a methodology of specifying the optical characteristics of prismatic intraocular lenses for a particular patient.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises a pair of intraocular lenses for restoring visual function to a patient with central field loss. The pair of intraocular lenses includes a first lens for implantation into a first eye of the patient to provide vision of targets located at a distance greater than five feet from the first eye and a second lens for implantation into a second eye of the patient to provide vision of targets at a distance less than twelve inches from the second eye. The first and second lenses each include a prismatic wedge for shifting retinal images to a functional portion of a retina of each respective first and second eye.

According to another aspect, the invention comprises a method of restoring visual function to a patient with central field loss. The method includes passing a first set of light rays through a first convex intraocular lens optic from a target located a distance greater than five feet from a first eye of the patient to focus the light rays. The focused first set of light rays passes through a first prismatic wedge located posterior to the first convex intraocular lens optic to redirect the focused first set of light rays to a functional portion of a retina of the first eye. A second set of light rays passes through a second convex intraocular lens optic from a target located a distance less than twelve inches from a second eye of the patient to focus the light rays. The focused second set of light rays passes through a second prismatic wedge located posterior to the second convex intraocular lens optic to redirect the focused second set of light rays to a functional portion of a retina of the second eye.

According to a further aspect, the invention comprises a lens for implantation into an eye. The lens includes a convex intraocular lens optic to focus a set of light rays, and a prismatic wedge located posterior to the lens optic to redirect the focused set of light rays to a functional portion of a retina of the eye. The magnitude of an angle of the prismatic wedge is determined according to the following formula:

$$\alpha = 360 d/2 \Pi a \, (n_1 - n_2)$$

where $\alpha$=the angle of the prismatic wedge;

d=a distance from the functional portion of the retina to a fovea of the eye;

$n_1$=a refractive index of the prismatic wedge;

$n_2$=a refractive index of an aqueous humor of the eye; and a=a distance from a posterior plane of the lens optic to the fovea.

It is to be understood that both the foregoing general description and the following detailed description are exemplary and explanatory only and are not restrictive of the invention, as claimed.

The accompanying drawings, which are incorporated in and constitute a part of this specification, illustrate an embodiment of the invention and together with the description, serve to explain the principles of the invention.

BRIEF DESCRIPTION OF THE DRAWINGS

FIG. 3 is a side elevation view of an intraocular lens and haptics according to the present invention; and FIG. 4 is a front elevation view of the intraocular lens of FIG. 3.

DESCRIPTION OF THE PREFERRED EMBODIMENT

Reference will now be made in detail to the present preferred embodiment of the invention, an example of which is illustrated in the accompanying drawings. Wherever possible, the same reference numbers will be used throughout the drawings to refer to the same or like parts.

The present invention is directed towards prismatic intraocular lenses and a related method of using such lenses to restore visual function to patients with central field loss. According to the invention, a first intraocular lens is provided in a first eye to provide vision of distant targets, those more than five feet away from the eye. A second intraocular lens is provided in the second eye of the patient to provide vision of targets within close range, about twelve inches or less from the eye and preferably within about three to nine inches from the eye.

Each intraocular lens includes a single refractive means to deflect the position of the image from a blind spot at the center of the eye, possibly a macular hole, to a functional area in the retina. Preferably, the single refractive means comprises a prismatic wedge integrally connected to a convex lens portion. Use of a single refractive means improves the total modulation transfer function delivered by the optic, in other words, improves the contrast versus resolution performance of the optic.

As discussed below, the present invention includes a method of accurately determining the prism wedge angle necessary for shifting a retinal image for particular patients. The thickness of the prismatic intraocular lens is also controlled by fabricating the lens from certain materials having specific indices of refraction, as also detailed below.

Figure 1:
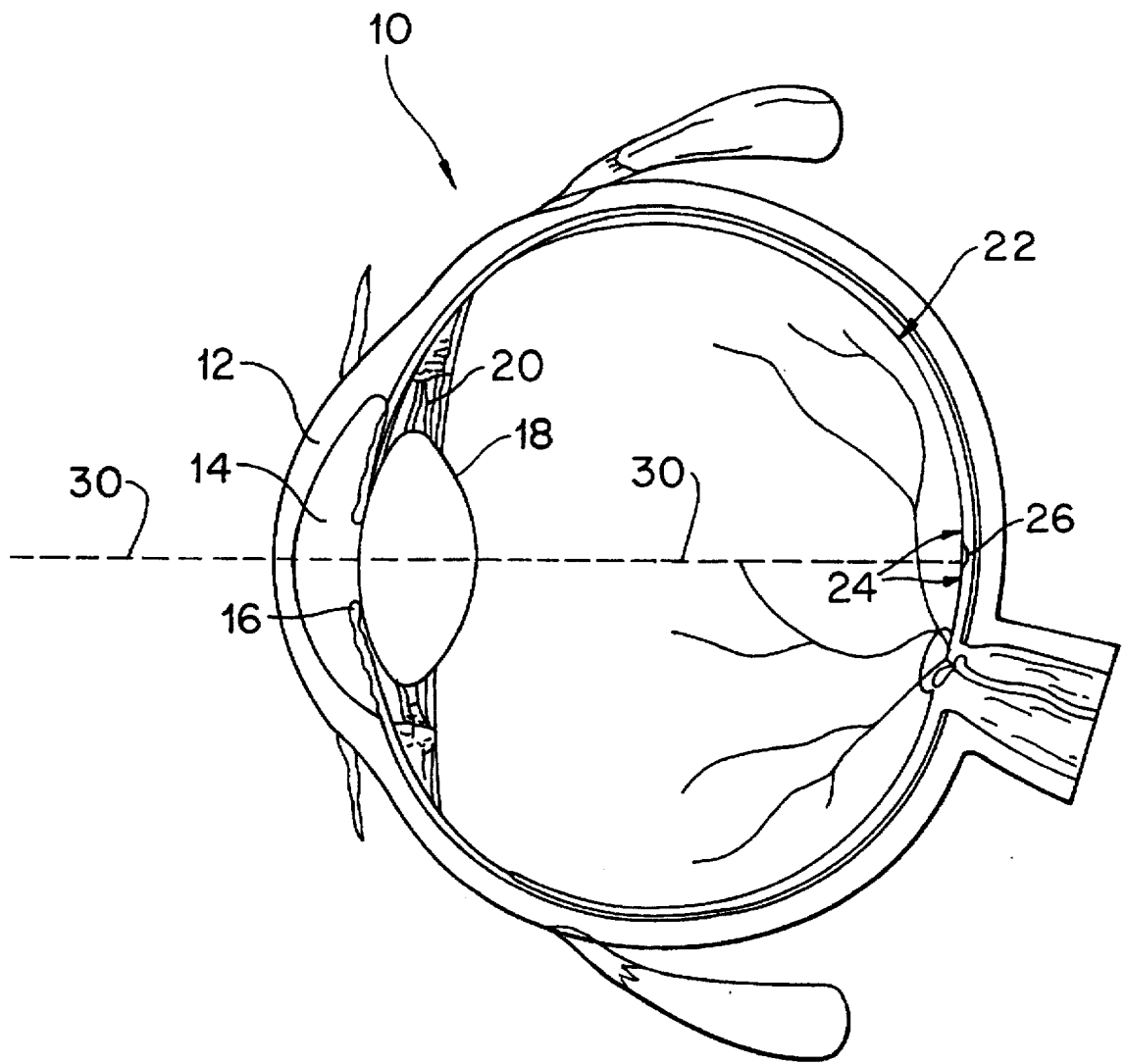
FIG. 1 is a side elevation sectional view of a normal human eye having a natural lens.
Figure 2:
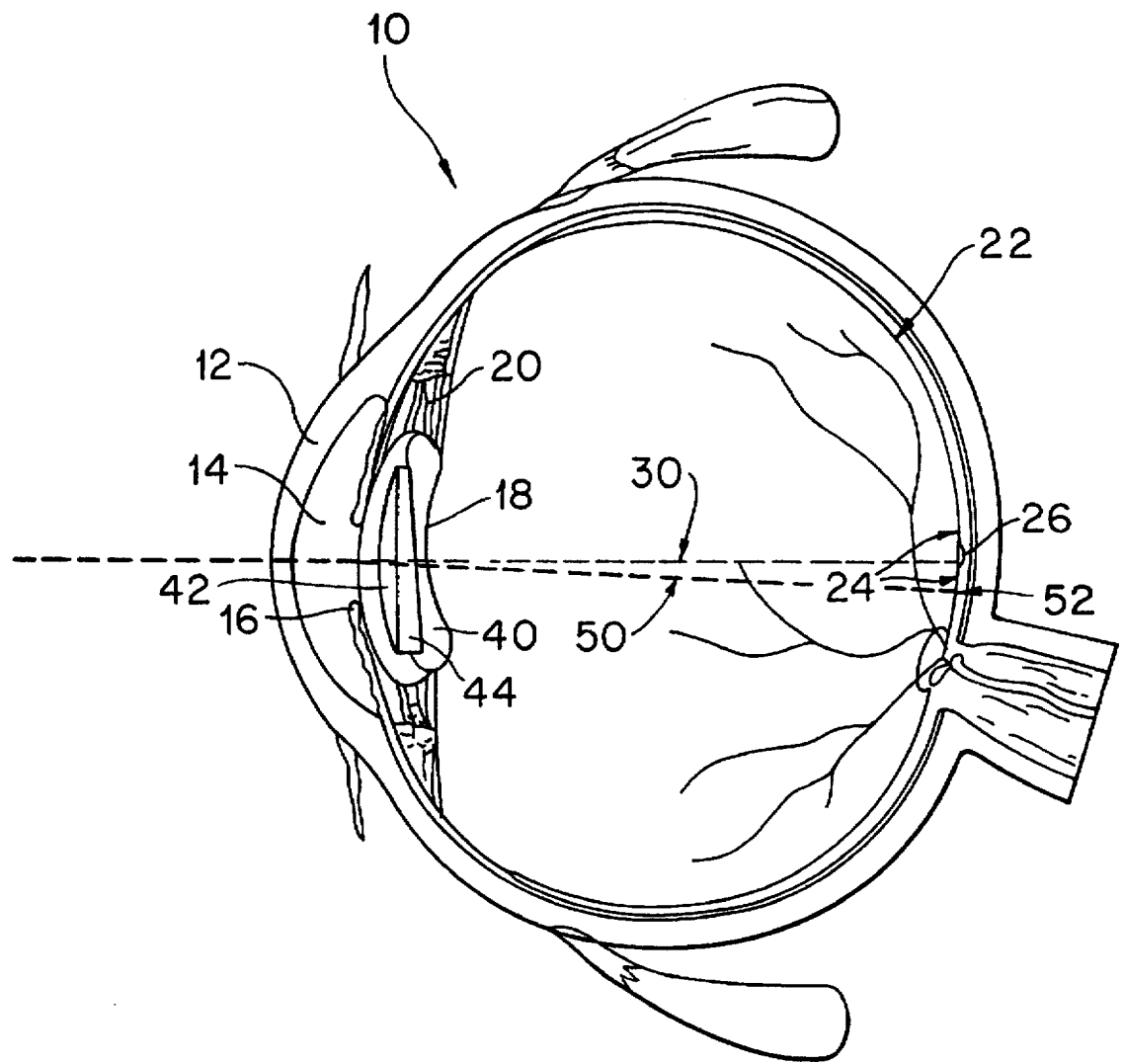
FIG. 2 is a side elevation sectional view of an eye incorporating a prismatic intraocular lens according to the present invention.

As shown in FIGS. 2 and 3, a prismatic intraocular lens 40 according to the present invention includes a convex lens portion 42 for focusing the image and a prism wedge 44 posterior to the lens portion for redirecting the image to a functional portion of the retina. As shown in FIG. 2, image 30 that forms at fovea 26 in a normal eye will be redirected to image 50 for shifting the image location to a healthy retinal area 52. A base portion 46 of the intraocular lens 40 defines the width and thickness of the haptics 48 that are described further herein.

A precise determination of the magnitude of angle $\alpha$ of prism wedge 44 is necessary to accurately shift the image to healthy retinal areas. In order to accurately determine prism wedge angle $\alpha$, a patient with visual impairment due to central field loss in both eyes is subjected to a series of diagnostic tests to determine the position of healthy, functional areas of the retina. Precise measurements are made to determine the distance from the fovea to the desired points of image fixation in each eye. Once functional areas are located, one eye is selected for vision of distant targets while the other is used for near vision.

The magnitude of angle $\alpha$ of prism wedge 44 for both lenses is then calculated according to the following formula:

$$\alpha = 360 d/2 \Pi a \, (n_1 - n_2)$$

where $\alpha$=magnitude of prism wedge angle in degrees;

d=the distance from the fovea to the desired healthy point of image fixation on the retina;

$n_1$=the refractive index of the prismatic intraocular lens material;

$n_2$=the refractive index of the aqueous solution in the aqueous humor, typically about 1.334; and a=the distance from the fovea to the posterior plane of the intraocular lens.

The distances d and a are determined form the patient's diagnostic tests. The refractive index $n_1$ of the prismatic intraocular lens is determined as described further below.

As a second step to sufficiently specify the intraocular lens optic for each eye, it is necessary to couple the magnitude of the prism wedge angle with the spherical power of each prismatic intraocular lens. The spherical power is the reciprocal of the focal length of the lens, and may be specified for best corrected distance vision or near vision. The spherical power of the intraocular lens depends on the length of the optic axis of the eye and the spherical power of the cornea. The optic axis of the eye is determined by ultrasonic imaging of the eye, a standard procedure preceding the removal of the crystalline lens of the eye and implantation of an intraocular lens. Corneal power is determined by measuring corneal curvature and corneal thickness, again through standard ultrasonic image scanning techniques.

As mentioned, the thickness of the prismatic intraocular lens according to the present invention must be controlled. For the preferred placement in the capsular sac, the maximum thickness of the lens is approximately 3.8 mm. Lenses thicker than 3.8 mm can be implanted into the ciliary sulcus. Implantation of the lens in the ciliary sulcus, anterior to the anterior lens capsule, can occur after performing a posterior capsulotomy followed by a vitrectomy. In such a case, or in the case of the implantation of the lens into the capsular fornix, the thickness of the lens should be controlled so as to not contact and thereby traumatize the iris.

Two methods may be used to minimize the thickness of the intraocular lens. First, aspheric optics reduce the intraocular lens thickness and also improve the quality of the retinal image by minimizing spherical aberration. In aspheric optics, the geometry of the lens surface (either anterior or posterior) is adjusted to correct for spherical aberration and to restore image contrast at the focal point. The corrected surface is aspheric in shape.

In a second method of reducing the thickness of the lens, the thickness of the prism wedge can be reduced by fabricating the prism wedge and convex lens portion from a material of high refractive index. The prism wedge angle required for a particular image shift decreases as the refractive index increases. The thickness of the prism wedge necessary for a particular image shift, therefore, decreases as the refractive index of the prism increases.

For various refractive indices, Table 1 shows the corresponding prism angles ($\alpha$) needed for a retinal shift d =1.0 mm when a=17 mm (the lens is positioned 17 mm from the fovea). The last column of Table 1 shows the increase in lens thickness that the prismatic wedge adds to a 6.0 mm diameter intraocular lens.

TABLE 1

| REFRACTIVE INDEX $n_1$ OF THE OPTIC MATERIAL | PRISM WEDGE ANGLE REQUIRED FOR 1.0 mm SHIFT, $\alpha$ (DEGREES) | ADDED THICKNESS TO A 6.0 mm DIAMETER INTRAOCULAR LENS (mm) |
|---|---|---|
| 1.50 | 20 | 2.2 |
| 1.56 | 14.7 | 1.6 |
| 1.60 | 12.5 | 1.3 |

As shown, by using a material of refractive index 1.6 as compared to one of refractive index 1.5, the overall thickness of the prismatic intraocular lens decreases by 0.9 mm.

A preferred material for 1-2 mm image shifts is polymethyl methacrylate (PMMA) having a refractive index of 1.498. For shifts greater than 2.0 mm, a material of higher refractive index should be used. An image shift of 3.0 mm or greater is rarely encountered since visual acuity drops steeply radially away from the fovea to as much as 20/200 or lower.

A material of refractive index in the range of 1.5–1.6 can be achieved through the polymerization of a suitable mixture of mono and/or multifunctional monomers and oligomers and a polymerization initiator. The polymerization can occur through an addition polymerization or a condensation polymerization process. Monomers and oligomers susceptible to addition polymerization include acrylates, methacrylates, styrenics, or allylic derivatives. Preferred examples of acrylate and methacrylate monomers for an addition polymerization reaction include phenyl ethyl acrylate, phenoxy ethyl acrylate, trifluoromethyl acrylate, ethyl acrylate, methyl methacrylate, and acrylic terminated organic phosphites and phosphine oxides. Preferred examples of acrylate and methacrylate oligomers for an addition polymerization reaction include polyethylene glycol diacrylate, polyethylene glycol dimethacrylate, aliphatic alkoxy diacrylate ester (code SR 9209 from Sartomer Corp.), bisphenol A diacrylate, and bisphenol A dimethacrylate. Expoxides, anhydrides, and silane derivative are among the preferred materials for condensation polymerization.

Combinations of these polymerizable derivatives produce biocompatible polymerizable formulations that form optically clear polymers with a refractive index in the range 1.5–1.6. The preferred selection of monomers and oligomers depends on biocompatibility as measured by standard toxicological tests, tissue compatibility, and lastly, when essential, implantation of intraocular lenses into the eyes of live animals.

The polymerization reactions of the preferred mixture may be carried out by the application of heat, light, or both. To fabricate the intraocular lens, the mixture may be either poured directly into molds shaped to form the lens, or formed into optical quality rods or sheets. The rods or sheets are then cored by a machining process to form buttons used in lens manufacture.

Each prismatic intraocular lens according to the present invention must be firmly supported and fixed within the eye to lessen its susceptibility to rotational displacement. Unwanted rotational displacement will potentially move the deflected image from a healthy retinal area to a dysfunctional area.

In the preferred embodiment, haptics 48, shown in FIGS. 3 and 4, are used to support and fix intraocular lens 40. The compressive force exerted by haptics 48 on the convex lens optic 42 prevents its rotational or tilting displacement and ensures its stability.

Preferably, each haptic 48 is integrally formed with the prismatic intraocular lens 10 to form a single piece construction. Each haptic 48 radiates out from the intraocular lens 10 in the form of a modified C. Haptics 48 may be formed from the same polymerizable materials described above for the lenses.

Because prismatic intraocular lenses 10 according to the present invention can weigh two to three times more than conventional intraocular lenses, and therefore require extra stability, haptics 48 must not be overly flexible. The trend in conventional haptic design is to decrease the compressive restoring force to as low as 80 mg of restoring force per millimeter of compression. According to the present invention, it has been found that a compressive restoring force for each haptic 48 is preferably in the range of 150–250 mg of restoring force per millimeter of compression, when measured with reference to overall relaxed dimensions. This higher restoring force increases the stability of the prismatic intraocular lens.

The axis joining the haptic-optic junction points is preferably located orthogonally to the prism axis. Such a configuration permits haptics of equal cross-section and easier polishing of the haptic-optic junction.

It will be apparent to those skilled in the art that various modifications and variations can be made in the prismatic intraocular lenses of the present invention and in construction of the prismatic intraocular lenses without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed:

1. A pair of intraocular lenses for restoring visual function to a patient with central field loss, the pair of intraocular lenses comprising:
   a first lens for implantation into a first eye of the patient to provide vision of targets located at a distance greater than five feet from the first eye; and
   a second lens for implantation into a second eye of the patient to provide vision of targets at a distance less than twelve inches from the second eye,
   wherein the first and second lenses each include a prismatic wedge for shifting retinal images to a functional portion of a retina of each respective first and second eye.

2. The pair of intraocular lenses according to claim 1, wherein the prismatic wedge of each of said first and second lenses is comprised of a material having a high refractive index.

3. The pair of intraocular lenses according to claim 2, wherein the prismatic wedge of each of said first and second lenses is comprised of a material having a refractive index in the range of approximately 1.5–1.6.

4. The pair of intraocular lenses according to claim 1, wherein a surface of the first lens and a surface of the second lens are corrected for spherical aberration.

5. The pair of intraocular lenses according to claim 1, wherein each of said first and second lenses is comprised of a polymerized mixture of monomers and oligomers.

6. The pair of intraocular lenses according to claim 5, wherein the monomers and oligomers include acrylates, methacrylates, styfenics, and allylic derivatives.

7. The pair of intraocular lenses according to claim 1, further comprising a plurality of haptics for securing each of said first and second lenses in the corresponding first and second eyes.

8. The pair of intraocular lenses according to claim 1, wherein the second lens provides vision of targets at a distance between about three inches and about nine inches from the second eye.

9. A pair of intraocular lenses for restoring visual function to a patient with central field loss, the pair of intraocular lenses comprising:
   a first lens for implantation into a first eye of the patient to provide vision of targets located at a distance greater than five feet from the first eye;
   a second lens for implantation into a second eye of the patient to provide vision of targets at a distanceless than twelve inches from the second eye; and
   a plurality of haptics for securing each of said first and second lenses in the corresponding first and second eyes;
   wherein the first and second lenses each include a prismatic wedge for shifting retinal images to a functional portion of a retina of each respective first and second eye, and each of said plurality of haptics has a compressive restoring force in the range of approximately 150–250 mg of restoring force per millimeter of compression.

10. The pair of intraocular lenses according to claim 9, wherein the second lens provides vision of targets at a distance between about three inches and about nine inches from the second eye.

11. A pair of intraocular lenses for restoring visual function to a patient with central field loss the pair of intraocular lenses comprising:
   a first lens for implantation into a first eye of the patient to provide vision of targets located at a distance greater than five feet from the first eye; and
   a second lens for implantation into a second eye of the patient to provide vision of targets at a distance less than twelve inches from the second eye,
   wherein the first and second lenses each include a prismatic wedge for shifting retinal images to a functional portion of a retina of each respective first and second eye, and a magnitude of an angle of the prismatic wedge for each of said first and second lenses is determined according to the following formula:

$$\alpha = 360 d/2\Pi a \, (n_1 - n_2)$$

where $\alpha$ = the angle of the prismatic wedge;
   $d$ = a distance from the functional portion of the retina to a fovea of each respective first and second eye;
   $n_1$ = a refractive index of each prismatic wedge;
   $n_2$ = a refractive index of an aqueous humor of each respective first and second eye; and
   $a$ = a distance from a posterior plane of each intraocular lens to the fovea of the corresponding eye.

12. The pair of intraocular lenses according to claim 11, wherein the second lens provides vision of targets at a distance between about three inches and about nine inches from the second eye.

13. A pair of lenses for restoring visual function to a patient with central field loss, the pair of intraocular lenses comprising:
   a first convex intraocular lens positioned in a first eye of the patient for receiving and focusing a first set of light rays from a target located a distance greater than five feet from the first eye;
   a first prismatic wedge located posterior to the first convex intraocular lens for receiving the focused first set of light rays and redirecting the focused first set of light rays to a functional portion of a retina of the first eye;
   a second convex intraocular lens positioned in a second eye of the patient for receiving and focusing a second set of light rays from a target located a distance less than twelve inches from the second eye; and
   a second prismatic wedge located posterior to the second convex intraocular lens for receiving the focused second set of light rays and redirecting the focused second set of light rays to a functional portion of a retina of the second eye.

14. The pair of lenses according to claim 13, wherein the second convex intraocular lens receives and focuses the second set of lights rays from a target located a distance between about three inches and about nine inches from the second eye.

15. A method of restoring visual function to a patient with central field loss comprising:
   passing a first set of light rays from a target located a distance greater than five feet from a first eye of the patient through a first convex intraocular lens optic positioned within the first eye to focus the light rays;
   passing the focused first set of light rays through a first prismatic wedge located posterior to the first convex intraocular lens optic to redirect the focused first set of light rays to a functional portion of a retina of the first eye;
   passing a second set of light rays from a target located a distance less than twelve inches from a second eye of the patient through a second convex intraocular lens optic positioned within the second eye to focus the light rays; and passing the focused second set of light rays through a second prismatic wedge located posterior to the second convex intraocular lens optic to redirect the focused first set of light rays to a functional portion of a retina of the second eye.

16. The method according to claim 15, wherein each prismatic wedge is comprised of a material having a high refractive index.

17. The method according to claim 16, wherein each prismatic wedge is comprised of a material having a refractive index in the range of approximately 1.5–1.6.

18. The method according to claim 15, wherein a surface of the first convex intraocular lens optic and a surface of the second convex intraocular lens optic are corrected for spherical aberration.

19. The method according to claim 15, wherein each of said first and second convex intraocular lens optics and each of said first and second prismatic wedges is comprised of a polymerized mixture of monomers and oligomers.

20. The method according to claim 19, wherein the monomers and oligomers include acrylates, methacrylates, styrenics, and allylic derivatives.

21. The method according to claim 15, wherein each of said first and second convex intraocular lens optics are integrally connected to each of said corresponding first and second prismatic wedges to form first and second integral lens structures, the first and second integral lens structures being secured to the corresponding first and second eyes by a plurality of haptics.

22. The method according to claim 21, wherein each of said plurality of haptics provides a compressive restoring force to each corresponding integral lens structure in the range of approximately 150–250 mg of restoring force per millimeter of compression.

23. The method according to claim 15, wherein the target is located a distance between about three inches and about nine inches from the second eye.

24. A method of restoring visual function to a patient with central field loss comprising:

passing a first set of light rays from a target located a distance greater than five feet from a first eye of the patient through a first convex intraocular lens optic positioned within the first eye to focus the light rays;

passing the focused first set of light rays through a first prismatic wedge located posterior to the first convex intretocular lens optic to redirect the for used first set of light rays to a functional portion of a retina of the first eye;

passing a second set of light rays from a target located a distance less than twelve inches from a second eve of the patient through a second convex intraocular lens optic positioned within the second eye to focus the light rays; and passing the focused second set of light rays through a second prismatic wedge located posterior to the second convex intraocular lens optic to redirect the focused first set of light rays to a functional portion of a retina of the second eye, wherein a magnitude of an angle of the first and second prismatic wedges is determined according to the following formula:

$$\alpha = 360d/2\Pi a\ (n_1 - n_2)$$

where $\alpha$=the angle of the prismatic wedge;

d=a distance from the functional portion of the retina to a fovea of each respective first and second eye;

$n_1$=a refractive index of each prismatic wedge;

$n_2$=a refractive index of an aqueous humor of each respective first and second eye; and a=a distance from a posterior plane of each intraocular lens to the fovea of the corresponding eye.

25. The method according to claim 12, wherein the target is located a distance between about three inches and about nine inches from the second eye.

26. A lens for implantation into an eye comprising:

a convex intraocular lens optic to focus a set of light rays; and a prismatic wedge located posterior to the lens optic to redirect the focused set of light rays to a functional portion of a retina of the eye, wherein a magnitude of an angle of the prismatic wedge is determined according to the following formula:

$$\alpha = 360d/2\Pi a\ (n_1 - n_2)$$

where $\alpha$=the angle of the prismatic wedge;

d=a distance from the functional portion of the retina to a fovea of the eye;

$n_1$=a refractive index of the prismatic wedge;

$n_2$=a refractive index of an aqueous humor of the eye; and a=a distance from a posterior plane of the lens optic to the fovea.

27. The lens according to claim 26, wherein the lens optic and prismatic wedge are comprised of a polymerized mixture of monomers and oligomers.

28. The lens according to claim 27, wherein the monomers and oligomers include acrylates, methacrylates, styrenics, and allylic derivatives.

29. The lens according to claim 26, further comprising a plurality of haptics for securing the lens in the eye, wherein each of said plurality of haptics has a compressive restoring force in the range of approximately 150–250 mg of restoring force per millimeter of compression.

30. A lens for implantation into an eye comprising:

a convex intraocular lens optic to focus a set of light rays;

a prismatic wedge located posterior to the lens optic to redirect the focused set of light rays to a functional portion of a retina of the eye; and a plurality of haptics for securing the lens in the eye, wherein each of said plurality of haptics has a compressive restoring force in the range of approximately 150–250 mg of restoring force per millimeter of compression.

31. The lens according to claim 27, wherein the prismatic wedge comprises a material having a refractive index in the range of approximately 1.5–1.6.

* * * * *

UNITED STATES PATENT AND TRADEMARK OFFICE
CERTIFICATE OF CORRECTION

PATENT NO. : 5,683,457

DATED : November 4, 1997

INVENTOR(S) : Amitava GUPTA et al.

It is certified that error appears in the above-identified patent and that said Letters Patent is hereby corrected as shown below:

Claim 9, column 7, line 45, "distanceless" should read --distance less--.

Claim 11, column 7, line 63, "loss the" should read --loss, the--.

Claim 24, column 9, line 43, "eve" should read --eye--;
                line 46, "introeocular" should read --intraocular--,
                       and "for used" should read --focused--;
                line 50, "eve" should read --eye--.

Title page, column 1, item [73], "Assignee: Prism Opthalmics, L.L.C."
                should read --Assignee: Prism Ophthalmics, L.L.C.--.

Signed and Sealed this

Sixth Day of January, 1998

Attest:

*Attesting Officer*

BRUCE LEHMAN

*Commissioner of Patents and Trademarks*